(12) United States Patent
Poirier et al.

(10) Patent No.: US 6,750,347 B2
(45) Date of Patent: Jun. 15, 2004

(54) SYNTHESIS OF INTERMEDIATES USEFUL IN PREPARING TRICYCLIC COMPOUNDS

(75) Inventors: Marc Poirier, Edison, NJ (US); Yee-Shing Wong, Florham Park, NJ (US); George G. Wu, Basking Ridge, NJ (US)

(73) Assignee: Schering-Corporation, Kenilworth, NJ (US)

( * ) Notice: Subject to any disclaimer, the term of this patent is extended or adjusted under 35 U.S.C. 154(b) by 0 days.

(21) Appl. No.: 10/174,145

(22) Filed: Jun. 18, 2002

(65) Prior Publication Data

US 2003/0050319 A1 Mar. 13, 2003

Related U.S. Application Data

(62) Division of application No. 09/836,605, filed on Apr. 17, 2001.
(60) Provisional application No. 60/198,341, filed on Apr. 18, 2000.

(51) Int. Cl.⁷ .............................................. C07D 221/22
(52) U.S. Cl. ........................................... 546/93; 546/79
(58) Field of Search ....................................... 546/79, 93

(56) References Cited

U.S. PATENT DOCUMENTS

| 4,282,233 A | 8/1981 | Vilani |
| 5,151,423 A | 9/1992 | Piwinski et al. |
| 5,998,620 A | * 12/1999 | Chen et al. |

FOREIGN PATENT DOCUMENTS

| WO | WO 98/42676 | 10/1998 |
| WO | WO 00/05215 | 2/2000 |
| WO | WO 00/30589 | 6/2000 |

OTHER PUBLICATIONS

R.D. Birkenmeyer et al., 1984, Journal of Medicinal Chemistry, 27:2 216–233.

* cited by examiner

*Primary Examiner*—Alan L. Rotman
*Assistant Examiner*—Binta Robinson
(74) *Attorney, Agent, or Firm*—William Y. Lee

(57) ABSTRACT

A process is provided for preparing a compound having the formula

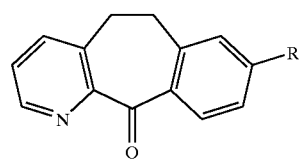

(I)

wherein R is H or Cl.

Also provided is a process for preparing a compound having the formula

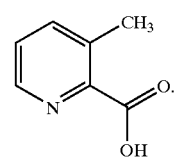

(VIII)

15 Claims, No Drawings

SYNTHESIS OF INTERMEDIATES USEFUL IN PREPARING TRICYCLIC COMPOUNDS

This application is a divisional of U.S. Ser. No. 09/836,605, filed on Apr. 17, 2001, which claims the benefit of U.S. Provisional Application No. 60/198,341, filed Apr. 18, 2000.

BACKGROUND OF THE INVENTION

This invention provides an improved process for preparing intermediates useful in the preparation of tricyclic compounds that are antihistamines. In particular, the compounds of this invention are useful in the preparation of antihistamines such as those disclosed in U.S. Pat. Nos. 4,282,233 and 5,151,423, especially loratadine and azatadine.

PCT Publication No. WO98/42676, published Oct. 1, 1998, discloses the following process for preparing tricyclic intermediates:

wherein R, $R^1$, $R^2$, $R^3$ and $R^4$ are independently selected from hydrogen or halo, $R^5$ and $R^6$ are independently selected from hydrogen, alkyl, aryl or heteroaryl, wherein $R^5$ and $R^6$ are not both hydrogen, and $R^7$ is Cl or Br. This process has some undesirable aspects, including the fact that carbon monoxide, a poisonous gas, must be used under high pressure to prepare the amide compound 2, and the fact that an expensive palladium catalyst must be used. The present invention provides an efficient process for preparing the tricyclic ketone that avoids these undesirable aspects.

SUMMARY OF THE INVENTION

This invention provides a process for preparing a compound having the formula

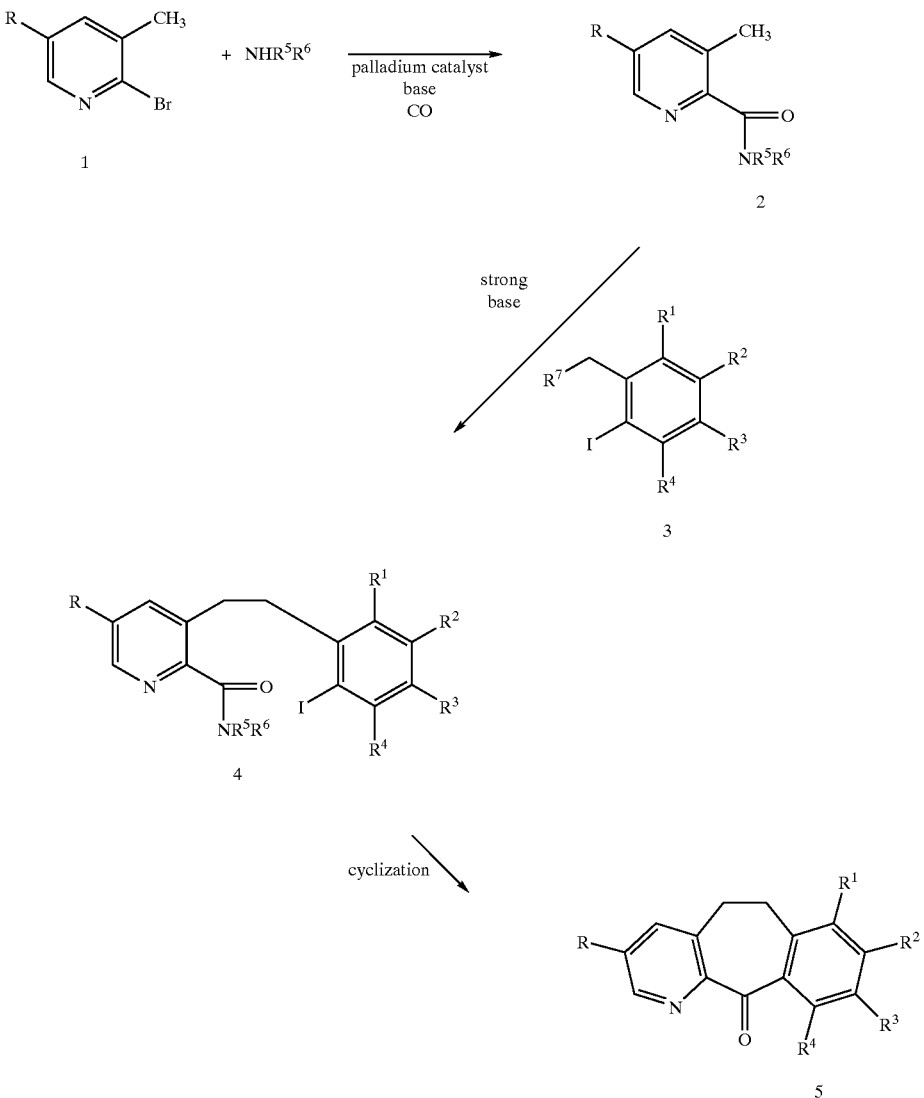

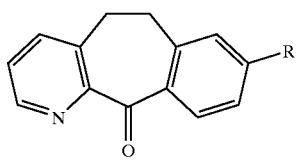
(I)

comprising:
(a) reacting a compound having the formula

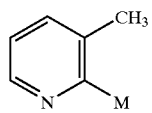
(II)

with an isocyanate having the formula R¹NCO to produce a compound having the formula

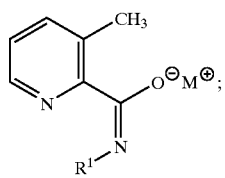
(III)

(b) optionally hydrolyzing the compound of formula (III) to form an amide having the formula

(IV)

(c) reacting the compound of formula (III) or the amide of formula (IV) with a compound having the formula

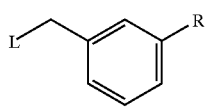
(V)

in the presence of a strong base to produce a compound having the formula

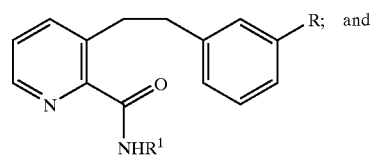
(VI) and (d) cyclizing the compound of formula (VI) to obtain the compound of formula (I), wherein R is H or Cl; M is selected from the group consisting of Li, Na, K, MgX, ZnR$^A$, and Al(R$^A$)$_2$; R$^A$ is alkyl; X is halo; R$^1$ is selected from the group consisting of alkyl, aryl, aralkyl, heteroaryl, heteroaralkyl, cycloalkyl, cycloalkylalkyl, heterocycloalkyl, and heterocycloalkylalkyl; and L is a leaving group.

This invention further provides a process for preparing a compound having the formula

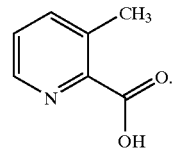
(VIII)

comprising reacting a compound having the formula

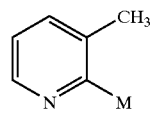
(II)

with $CO_2$ and a protonating agent to obtain the compound of formula (VIII), wherein M is selected from the group consisting of Li, Na, K, MgX, ZnR$^A$, and Al(R$^A$)$_2$, wherein R$^A$ is alkyl and X is halo.

DETAILED DESCRIPTION

As used herein, the term "alkyl" means straight or branched hydrocarbon chains of 1 to 10 carbon atoms, preferably 1 to 6 carbon atoms, optionally substituted by one or more substituents selected from $C_1$ to $C_6$ alkoxy, halo, or $CF_3$.

"Alkoxy" means a group having the formula —O-alkyl.

"Halo" refers to fluorine, chlorine, bromine or iodine radicals.

"Aryl" means phenyl or a polyaromatic ring (e.g., napthyl) optionally substituted by one or more substituents selected from the group consisting of $C_1$ to $C_6$ alkyl, $C_1$ to $C_6$ alkoxy, halo, or $CF_3$.

"Aralkyl" means a group having the formula —R-aryl, wherein R is alkyl;

"Heteroaryl" means a 5- or 6-membered aromatic ring having one or two nitrogen atoms (e.g., pyridyl, pyrimidyl, imidazolyl or pyrrolyl), optionally substituted by one or more substituents selected from the group consisting of $C_1$ to $C_6$ alkyl, $C_1$ to $C_6$ alkoxy, halo, or $CF_3$;

"Heteroaralkyl" means a group having the formula —R-heteroaryl, wherein R is alkyl;

"Cycloalkyl" means a non-aromatic carbocyclic ring of from 3 to 6 carbon atoms, optionally substituted by one or more substituents selected from the group consisting of $C_1$ to $C_6$ alkyl, $C_1$ to $C_6$ alkoxy, halo, or $CF_3$;

"Cycloalkylalkyl" means a group having the formula —R-cycloalkyl, wherein R is alkyl;

"Heterocycloalkyl" means a 3 to 6 membered non-aromatic ring having from 1 to 3 heteroatoms selected from O, S and N, wherein the remaining members of the ring are carbon atoms, optionally substituted by one or more substituents selected from the group consisting of $C_1$ to $C_6$ alkyl, $C_1$ to $C_6$ alkoxy, halo, or $CF_3$;

"Heterocycloalkylalkyl" means a group having the formula —R-heterocycloalkyl, wherein R is alkyl.

R is preferably Cl.

M is preferably selected from Li, Na, K, and MgX.

$R^1$ is preferably alkyl or aryl. $R^1$ is most preferably t-butyl, phenyl or 4-chlorophenyl.

Examples of suitable leaving groups, L, include, but are not limited to Cl, Br, I, alkyl sulfonates, aryl sulfonates, dialkyl phosphates, diaryl phosphates and $R^BOC(O)O-$, wherein $R^B$ is alkyl or aryl. L is preferably selected from Cl, Br, mesylate, tosylate, brosylate, triflate, and $-OP(OC_2H_5)_2$.

Certain substituents, solvents and reagents are referred to herein by the following abbreviations: lithium diisopropylamide (LDA); n-butyl lithium (n-BuLi); tetrahydrofuran (THF); and phenyl (Ph).

The compounds of formula (I) prepared by the present process are useful as intermediates in the procedures described in U.S. Pat. No. 5,151,423 to obtain the desired compounds wherein the piperidinyl ring is N-substituted. Using those procedures, the compounds of formula (I) may be reacted with a substituted piperidine of the formula

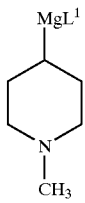

wherein $L^1$ is Cl or Br, to obtain a compound of the formula

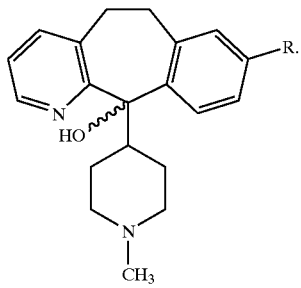

This compound is converted to the corresponding piperidylidene, the nitrogen is deprotected, and the compound is reduced to the piperidyl form. The piperidinyl nitrogen can then be reacted with a variety of compounds, e.g., an acyl compound such as an ester or acyl chloride to form the desired amide.

The compound of formula (VIII) produced in accordance with our invention can be used to prepare the amide of formula (IV) by reacting it with an organic base, e.g., triethylamine, followed by an acid chloride, e.g., pivaloyl chloride or a chloroformate, e.g., $C_2H_5OCOCl$ in a suitable solvent such as dichloromethane at a temperature of about $-30°$ C. to $0°$ C. to give a mixed anhydride, and reacting the mixed ahydride with an amine of the formula $NH_2R^1$ at a temperature of $-30°$ C. to $0°$ C. to form the amide of formula (IV).

Those skilled in the art will recognize that the compound represented by formula (III) exhibits resonance as shown below:

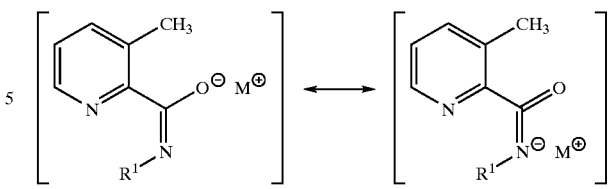

As used herein, the compound of formula (III) is intended to represent both of these resonance structures, as well as the resonance hybrid of these structures.

The starting compounds of formula (II) are either known in the art, or can be readily prepared by one skilled in the art, using conventional methods. Preferably, the starting compounds of formula (II) are prepared in situ from a 2-halo 3-methyl pyridine, e.g., 2-bromo 3-methyl pyridine. For example, when M is Li, Na, or K, the compound of formula (II) can be prepared by reacting 2-bromo 3-methyl pyridine with an alkyl or aryl lithium, sodium or potassium compound, preferably an n-butyl lithium, sodium or potassium. When M is MgX, the compound of formula (II) can be prepared by reacting 2-bromo 3-methyl pyridine with an alkyl or aryl Grignard. When M is $ZnR^A$ or $Al(R^A)_2$, the compound of formula (II) can be prepared by reacting 2-bromo 3-methyl pyridine with $Zn(R^A)_2$ or $Al(R^A)_3$.

In step (a) of the present process, the compound of formula (II) is reacted with an isocyanate having the formula $R^1NCO$ to produce the compound of formula (III). Preferably, the amount of isocyanate used in step (a) is 1.0 to 2.0 equivalents, more preferably, 1.0 to 1.5 equivalents, most preferably 1.0 to 1.1 equivalents. The reaction of step (a) is preferably carried out in an organic solvent, more preferably an aprotic organic solvent. Examples of suitable solvents, include, but are not limited to THF, ethylene glycol dimethyl ether, diethyl ether, methyl t-butyl ether, N,N,N',N'-tetramethylethylenediamine, and mixtures thereof. THF, N,N, N',N'-tetramethylethylenediamine, and mixtures of THF and ethylene glycol dimethyl ether are particularly preferred. Step (a) is preferably carried out at a temperature of $-110$ to $-40°$ C., more preferably $-90$ to $-60°$ C., most preferably $-80$ to $-70°$ C.

Optionally, the compound of formula (III) may be hydrolyzed to form the amide of formula (IV) (step (b)). The optional hydrolysis is preferably carried out by quenching the reaction mixture from step (a) with a saturated aqueous solution of ammonium chloride. Alternatively, dilute HCl or dilute sulfuric acid could be used instead of ammonium chloride. The hydrolysis is preferably carried out at a temperature of $-20$ to $20°$ C., more preferably $-10$ to $10°$ C., most preferably 0 to $5°$ C.

In step (c), the compound of formula (III) or the amide of formula (IV) is reacted with the compound of formula (V) in the presence of a strong base to produce the compound of formula (VI). Examples of strong bases include, but are not limited to: butyl lithium, lithium diisopropylamide (LDA), lithium hexamethyldisilylamide, and sodium amide. The strong base is preferably butyl lithium or LDA. Preferably, the amount of strong base used in step (c) is 2.0 to 2.5 equivalents, more preferably, 2.0 to 2.2 equivalents, most preferably 2.0 to 2.05 equivalents. Preferably, the amount of compound (V) used in step (c) is 1.0 to 1.5 equivalents, more preferably, 1.0 to 1.2 equivalents, most preferably 1.0 to 1.1 equivalents. Step (c) is preferably carried out at a temperature of $-80$ to $20°$ C., more preferably $-60$ to $-10°$ C., most preferably $-40$ to $-30°$ C.

In a particularly preferred embodiment, step (b) is not carried out, and the product produced in step (a) is not isolated prior to carrying out step (c), i.e., steps (a) and (c) are carried out as a one-pot process.

In step (d), the compound of formula (VI) is cyclized to obtain the compound of formula (I). The cyclization is preferably carried out in an organic solvent, preferably an aprotic organic solvent. The aprotic organic solvent is preferably selected from dichloroethane, methylene chloride, benzene, and halogenated aromatic solvents, e.g., chlorobenzene, dichlorobenzene, trichlorobenzene, and trifluoromethylbenzene.

Preferably, the cyclization is carried out by reacting the compound of formula (VI) with a dehydrating agent to produce an imine having the formula:

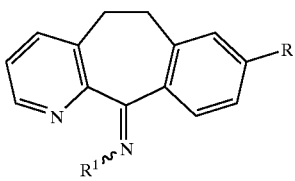

(VII)

and hydrolyzing the imine of formula (VII) to produce the compound of formula (I). The dehydrating agent is preferably selected from the group consisting of $P_2O_5$, $P_2O_3$, $P_2O_3Cl_4$, $POCl_3$, $PCl_3$, $PCl_5$, $C_6H_5P(O)Cl_2$ (phenyl phosphonic dichloride), $PBr_3$, $PBr_5$, $SOCl_2$, $SOBr_2$, $COCl_2$, $H_2SO_4$, super acids, and anhydrides of super acids. More preferably, the dehydrating agent is selected from $P_2O_5$, $P_2O_3Cl_4$, $PBr_3$, $PCl_5POCl_3$, $C_6H_5P(O) Cl_2$, $(CF_3SO_2)_2O$, and $(CF_3CF_2SO_2)_2O$.

The reaction of compound (VI) with the dehydrating agent is preferably carried out at a temperature of 10 to 120° C., more preferably, 15 to 90° C., most preferably 20 to 90° C. The time for reaction ranges from 1 to 60 hours, preferably 2 to 40 hours, most preferably 5 to 35 hours.

It is particularly preferred to form the imine by contacting the reaction mixture of the compound of formula (VI) and the dehydrating agent with an additional agent selected from the group consisting of a Lewis acid or a super acid. Examples of Lewis acids include $AlCl_3$, $FeCl_3$, $ZnCl_2$, $AlBr_3$, $ZnBr_2$, $TiCl_4$, and $SnCl_4$. Of the foregoing, $AlCl_3$, $FeCl_3$, $ZnCl_2$, and $ZnBr_2$ are particularly preferred. Examples of super acids include $CF_3SO_3H$,

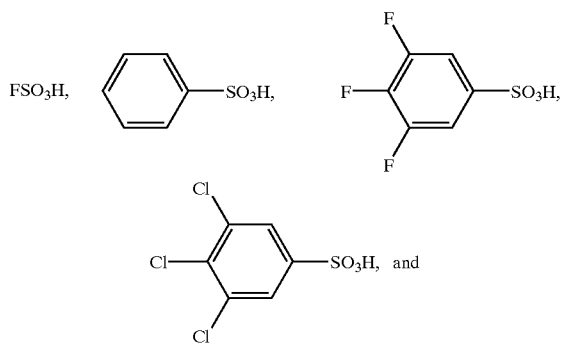

$HF/BF_3$. Of the foregoing super acids, $CF_3SO_3H$ is particularly preferred. The contacting by the Lewis acid or the super acid may be accomplished by adding it prior to, contemporaneously with, or after the time at which the dehydrating agent is brought into contact with the compound of formula (VI). Particularly preferred combinations of dehydrating agents and Lewis acids or super acids include $P_2O_5/CF_3SO_3H$, $PCl_5/AlCl_3$, $PCl_5/FeCl_3$, $POCl_3/ZnCl_2$, and $POCl_3/ZnBr_2$.

When a dehydrating agent other than an anhydride is used, preferably the dehydrating agent is used in amounts ranging from 1.0 to 20 equivalents, more preferably, 1.0 to 10 equivalents, most preferably, 1.0 to 8.0 equivalents. When the dehydrating agent is an anhydride of a super acid, it is preferably used in amounts ranging from 0.5 to 10 equivalents, more preferably 1.0 to 5.0 equivalents, most preferably, 1.2 to 2.0 equivalents. When a Lewis acid is used in addition to the dehydrating agent, the Lewis acid is preferably used in amounts ranging from 1 to 20 equivalents, more preferably 1.5 to 10 equivalents, most preferably 2 to 5 equivalents. When a super acid is used in addition to the dehydrating agent, the super acid is preferably used in amounts ranging from 0.5 to 10 equivalents, more preferably, 1 to 5 equivalents, most preferably, 2 to 4 equivalents.

The imine of formula (VII) is preferably hydrolyzed by adding water, preferably in an amount ranging from 1 to 10 volumes relative to the amount of the compound of formula (VI) used, more preferably 1.5 to 7 volumes, most preferably 2 to 5 volumes. The hydrolysis is preferably carried out at a temperature of from 20 to 120° C., more preferably from 30 to 100° C., most preferably from 40 to 80° C.

The process for converting the compound of formula (II) into the compound of formula (VIII) is carried out by reacting the compound of formula (II) with $CO_2$ and a protonating agent to form the compound of formula (VIII). The reaction is preferably carried out at a temperature of −110 to 0° C., more preferably −80 to −20° C., most preferably −60 to −40° C. The protonating agent is preferably water or an acid. Preferably, the $CO_2$ is in the form of dry ice or as a gas. Preferably, the amount of $CO_2$ used is 1 to 10 equivalents, more preferably, 1 to 5 equivalents, most preferably 1 to 2 equivalents. Most preferably, the compound of formula (II) is reacted with the $CO_2$ in an organic solvent, and the reaction mixture is protonated by quenching it with water.

The isocyanate ($R^1NCO$) and the compound of formula (V) used in the foregoing processes are either known compounds or can be readily prepared by one skilled in the art using known methods.

Those skilled in the art will appreciate that unless stated otherwise, the compounds produced in the various process steps can, if desired, be separated from their reaction mixtures, and isolated and purified by techniques well known in the art. For example, separation can be accomplished by precipitation, chromatography (e.g., column), phase separation (extraction) and distillation. The desired product can then be dried and purified by recrystallization.

The following examples illustrate the foregoing invention, although such examples should not be construed as limiting the scope of the invention. Alternative reagents and analagous processes within the scope of the invention will be apparent to those skilled in the art.

EXAMPLE 1

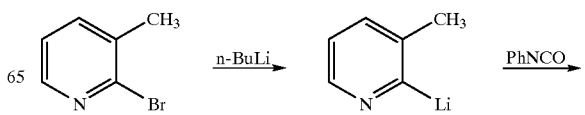

-continued

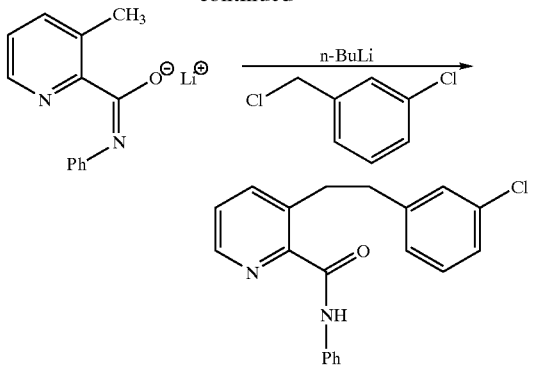

To a −55° C. solution of 2-bromo 3-methyl pyridine (5 g, 27.6 mmole) in THF (50 mL) was added n-Buthyl lithium (2.5M in hexanes, 11.0 mL, 27.6 mmole) dropwise. After 5 minutes, phenyl isocyanate (29.0 mmole, 3.1 mL) was added dropwise. The mixture was stirred at −55° C. for 10 minutes and a second equivalent of n-Buthyl lithium (2.5M in hexanes, 11.0 mL, 27.6 mmole) was added dropwise. The mixture was sitrred at −55° C. for 10 minutes and 3-chlorobenzyl chloride (3.6 mL, 27.6 mmole) was added dropwise. The temperature was allowed to warm to 25° C. and the reaction was quenched into a saturated aqueous solution of ammonium chloride (50 mL). The product was extracted twice with ethyl acetate (20 ml). The product yield in the combined organic solution was estimated by HPLC (1.8 g, 20%). The crude product was also analyzed by $^1$H NMR and compared with an authentic sample of product. $^1$H NMR (CDCl$_3$): δ 10.23 (s, 1H), 8.48 (dd, J=4.6, 1.6 Hz, 1H), 7.78 (dd, J=0.8, 8.4 Hz, 2H), 7.48 (dd, J=7.9, 1.5 Hz, 1H), 7.12–7.39 (m, 8H), 3.50–3.54 (m, 2H), 2.98–3.02 (m, 2H).

EXAMPLE 2

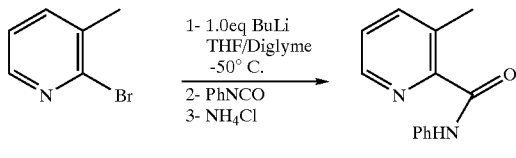

n-Butyl lithium (2.5M in hexanes, 12.0 ml, 30.4 mmole) was added to THF (40 ml) and ethylene glycol dimethyl ether (2.5 ml) at −50° C. A solution of 2-bromo 3-methyl pyridine (5 g, 27.6 mmole) in THF (10 ml) was added dropwise over a period of 5 minutes to the n-buthyl lithium solution at −50° C. After 15 minutes, phenyl isocyanate (31.8 mmole, 3.5 ml) was added dropwise over a period of 5 minutes while the temperature raised to −45° C. The mixture was allowed to warm to −10° C. and was quenched into 50 ml of a saturated aqueous solution of ammonium chloride. The product was extracted twice with t-butyl methyl ether (50 ml). The combined organic solution was dried over MgSO$_4$ and concentrated to dryness. The crude product was then purified by filtration on silica gel to give 5.1 g (88%) of white solid. m.p. 66–67° C. $^1$H NMR (CDCl$_3$): δ 10.23 (bs, 1H), 8.37 (dd, J=4.6, 0.8 Hz, 1H), 7.71 (m, 2H), 7.62 (dd, J=6.9 Hz, 1H), 7.31–7.36 (m, 3H), 7.10 (t, J=7.4 Hz, 1H), 2.79 (s, 3H). $^{13}$C NMR (CDCl$_3$): δ 163.5, 146.7, 145.2, 141.2, 138.0, 136.1, 128.9, 125.9, 123.9, 119.6, 20.8.

EXAMPLE 3

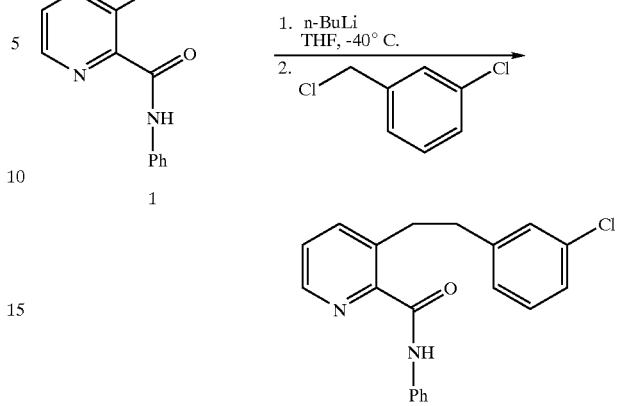

To a −40° C. solution of the compound of formula 1 (20 g, 92.45 mmole) in THF (200 mL) was added a 2.5M solution of Butyllithium in Hexanes (74 mL, 190 mmole) dropwise. After 5 minutes, the resulting dianion solution was quenched with 3-Chlorobenzylchloride (12.5 mL, 97.0 mmole). The mixture was allowed to warm to 0° C. and, after 1 hour, was quenched into a saturated aqueous solution of NH$_4$Cl (200 mL). The phases were separated and the aqueous layer was extracted with tert-Butyl methyl ether (100 mL). Concentration of the solvent and crystalization in isopropyl alcohol (60 mL) gave 27.0 g (86.1%) of the coupled product. Mp.80–81° C. $^1$H NMR (CDCl$_3$): δ 10.23 (s, 1H), 8.48 (dd, J=4.6 Hz, 1.6 Hz, 1H), 7.78 (dd, J=0.8 Hz, 8.4 Hz, 2H), 7.48 (dd, J=7.9 Hz, 1.5 Hz, 1H), 7.12–7.39 (m, 8H), 3.50–3.54 (m, 2H), 2.98–3.02 (m, 2H). $^{13}$C NMR (CDCl$_3$): δ 164.09, 147.63, 146.72, 144.63, 141.91, 140.16, 138.97, 134.98, 130.55, 130.05, 129.82, 128.03, 127.16, 127.03, 125.17, 120.84, 38.30, 36.77. IR: 2930 (s), 1690 (m) cm$^{-1}$.

EXAMPLE 4

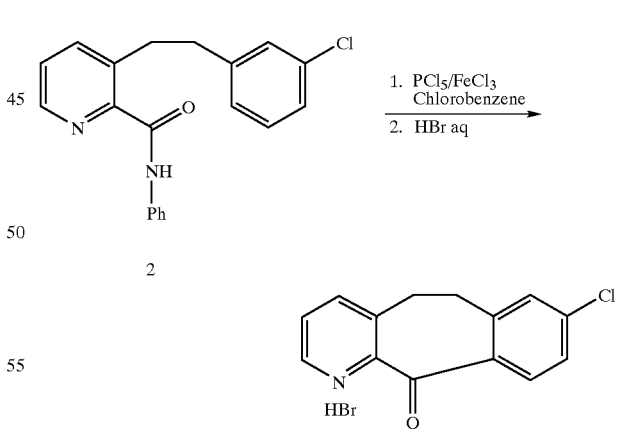

The compound of formula 2 (15 g, 43.7 mmole) was dissolved in chlorobenzene (45 ml) at 25° C. Phosphorus pentachloride (11.8 g, 56.9 mmole) was added and the mixture was stirred at 35° C. for 2 hours. The resulting thick suspension was cooled to 10° C. and iron (III) chloride (10.6 g, 65.6 mmole) was added portionwise while maintaining the temperature below 30° C. The solution was slowly heated to 85° C. and stirred over-night under a nitrogen flow.

The reaction mixture was cooled to 25° C. and poured into a brine solution (60 g/250 ml). The product was extracted with ethyl acetate (60 ml). After the phase separation, the organic layer was washed twice with a brine solution (45 g/200 ml). The organic solution was then filtered and diluted with acetone (15 ml). A 48% solution of hydrobromic acid in water (8 ml) was added and the mixture was stirred at 25° C. for 16 hours. The product was filtered as a salt and dried at 50° C. in a vaccum oven to give 8.3 g (59%). m.p. 261–263° C. $^1$H NMR (DMSO-d$_6$): δ 8.93 (dd, J=5.3, 1.3 Hz, 1H), 8.57 (dd, J=7.9, 1.1 Hz, 1H), 8.11 (d, J=7.9 Hz, 1H), 8.10 (d, J=8.5 Hz, 1H), 7.68 (d, J=2.1 Hz, 1H), 7.63 (dd, J=8.5, 2.1 Hz, 1H), 3.40 (m, 4H). $^{13}$C NMR (DMSO-d$_6$): δ 186.1, 147.2, 145.4, 145.1, 143.9, 141.8, 139.3, 134.3, 133.7, 130.1, 129.5, 127.6, 32.7, 32.0.

EXAMPLE 5

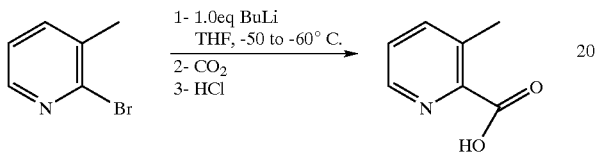

To a −55° C. solution of 2-bromo 3-methyl pyridine (5 g, 27.6 mmole) in THF (50 ml) was added a 2.5 M solution of n-buthyl lithium in hexanes (11.0 ml, 27.6 mmole). After 10 minutes, 12 g of dry ice pellets (CO$_2$) were added to the mixture. The temperature was then raised to 25° C. The reaction was quenched into water (250 ml) and extracted with ethyl acetate. The aqueous layer was neutralised to pH between 5 and 6 with 3.0 N hydrochloric acid and concentrated to dryness. The crude product (3.6 g) was analyzed by NMR. $^1$H NMR (D$_2$O): δ 8.10 (d, J=3.8 Hz, 1H), 7.63 (d, J=7.7 Hz, 1H), 7.22 (dd, J=5.9, 6.9 Hz, 1H), 2.19 (s, 3H). $^{13}$C NMR (D$_2$O): δ 174.9, 155.0, 144.8, 141.9, 131.2, 125.1, 18.6.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for preparing a compound having the formula

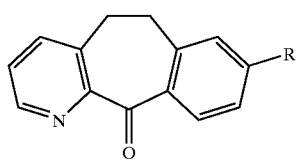

comprising:
(a) reacting a compound having the formula

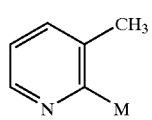

with an isocyanate having the formula R$^1$NCO to produce a compound having the formula

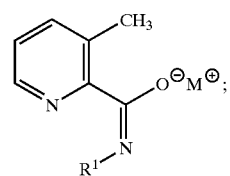

(b) optionally hydrolyzing the compound of formula (III) to form an amide having the formula

(c) reacting the compound of formula (III) or the amide of formula (IV) with a compound having the formula

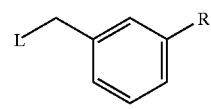

in the presence of a strong base to produce a compound having the formula

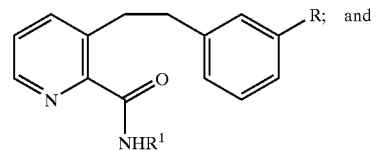

(d) cyclizing the compound of formula (VI) to obtain the compound of formula (I), wherein R is H or Cl; M is selected from the group consisting of Li, Na, K, MgX, ZnR$^A$, and Al(R$^A$)$_2$, R$^A$ is alkyl; X is halo; R$^1$ is selected from the group consisting of heteroaryl, heterocycloalkyl, and heterocycloalkylalkyl and L is a leaving group.

2. The process of claim 1, wherein R is Cl.

3. The process of claim 2, wherein M is selected from the group consisting of Li, Na, K, and MgX.

4. The process of claim 1 wherein the optional step (b) is not carried out, and wherein the compound produced in step (a) is not isolated prior to carrying out step (c).

5. The process of claim 4, wherein L is selected from the group consisting of Cl, Br, I, alkyl sulfonates, aryl sulfonates, dialkyl phosphates, diaryl phosphates and R$^B$OC(O)O—, wherein R$^B$ is alkyl or aryl.

6. The process of claim 5, wherein L is selected from Cl, Br, mesylate, tosylate, brosylate, triflate, and —OP(OC$_2$H$_5$)$_2$.

7. The process of claim 5, wherein the cyclization is carried out by treating the compound of formula (VI) with a dehydrating agent to form an imine having the formula

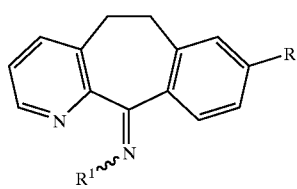

(VII)

and the imine is hydrolyzed to form the compound of formula (I).

8. The process of claim 7, wherein the dehydrating agent is selected from $P_2O_5$, $P_2O_3$, $P_2O_3Cl_4$, $POCl_3$, $PCl_3$, $PCl_5$, $C_6H_5P(O)Cl_2$, $PBr_3$, $PBr_5$, $SOCl_2$, $SOBr_2$, $COCl_2$, $H_2SO_4$, super acids, and anhydrides of super acids.

9. The process of claim 8, wherein the treatment with the dehydrating agent is carried out in the presence of an additional agent selected from the group consisting of a Lewis acid or a super acid.

10. The process of claim 9, wherein the additional agent is selected from the group consisting of $AlCl_3$, $FeCl_3$, $ZnCl_2$, $AlBr_3$, $ZnBr_2$, $TiCl_4$, $SnCl_4$, $CF_3SO_3H$,

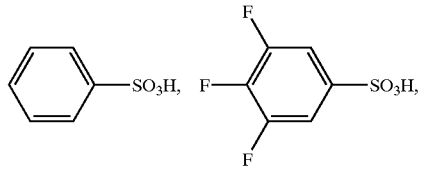

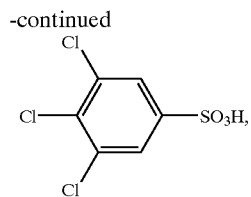

$FSO_3H$, and $HF/BF_3$.

11. The process of claim 10, wherein the dehydrating agent is selected from the group consisting of $P_2O_5$, $P_2O_3Cl_4$, $PBr_3$, $PCl_5$, $POCl_3$, $C_6H_5P(O)Cl_2$, $(CF_3SO_2)_2O$, and $(CF_3CF_2SO_2)_2O$, and the additional agent is selected from the group consisting of $AlCl_3$, $FeCl_3$, $ZnCl_2$, $ZnBr_2$, and $CF_3SO_3H$.

12. The process of claim 1, wherein R is H, M is selected from the group consisting of Li, Na, K, and MgX, and $R^1$ is t-butyl, phenyl or 4-chlorophenyl.

13. The process of claim 12, wherein the optional step (b) is not carried out, and wherein the compound produced in step (a) is not isolated prior to carrying out step (c).

14. The process of claim 13, wherein L is selected from the group consisting of Cl, Br, I, alkyl sulfonates, aryl sulfonates, dialkyl phosphates, diaryl phosphates and $R^BOC(O)O-$, wherein $R^B$ is alkyl or aryl.

15. The process of claim 14, wherein L is selected from Cl, Br, mesylate, tosylate, brosylate, triflate, and $-OP(OC_2H_5)_2$.

* * * * *